United States Patent
Katsumoto et al.

(10) Patent No.: US 7,070,605 B2
(45) Date of Patent: Jul. 4, 2006

(54) GREAT SAPHENOUS VEIN VARIX TREATMENT TOOL

(75) Inventors: Keiichiro Katsumoto, Tokyo (JP); Tadashi Yokokura, Kanagawa (JP)

(73) Assignee: Tsukada Medical Research Co., Ltd., Tokyo (JP)

( * ) Notice: Subject to any disclaimer, the term of this patent is extended or adjusted under 35 U.S.C. 154(b) by 44 days.

(21) Appl. No.: 10/381,275

(22) PCT Filed: Jun. 25, 2001

(86) PCT No.: PCT/JP01/05390

§ 371 (c)(1), (2), (4) Date: Mar. 24, 2003

(87) PCT Pub. No.: WO03/000143

PCT Pub. Date: Jan. 3, 2003

(65) Prior Publication Data

US 2003/0176882 A1    Sep. 18, 2003

(51) Int. Cl.
*A61B 17/00* (2006.01)

(52) U.S. Cl. ...................... 606/190; 606/224

(58) Field of Classification Search ............... 128/899; 604/19; 623/1.1; 606/222, 224, 228, 72, 606/74; 206/63.3
See application file for complete search history.

(56) References Cited

U.S. PATENT DOCUMENTS 3,749,238 A * 7/1973 Taylor ..................... 206/227
3,877,570 A * 4/1975 Barry ..................... 206/63.3
4,168,000 A * 9/1979 MacRitchie ............... 206/63.3
5,368,595 A * 11/1994 Lewis ........................ 606/72
5,383,901 A * 1/1995 McGregor et al. .......... 606/223
5,423,821 A * 6/1995 Pasque ....................... 606/74
5,454,834 A * 10/1995 Boebel et al. ............. 606/228
6,016,905 A * 1/2000 Gemma et al. ............ 206/63.3
6,161,695 A * 12/2000 Nicolais ..................... 206/438
6,322,570 B1 * 11/2001 Matsutani et al. .......... 606/145
6,475,229 B1 * 11/2002 Pagedas ..................... 606/228
6,607,541 B1 * 8/2003 Gardiner et al. ............ 606/151

FOREIGN PATENT DOCUMENTS

| EP | 882428 A2 | 12/1998 |
|----|-----------|---------|
| JP | 2000-28114 A | 10/2000 |
| JP | 2001 58009 A | 3/2001 |

* cited by examiner

*Primary Examiner*—Corrine McDermott
*Assistant Examiner*—Christopher Prone
(74) *Attorney, Agent, or Firm*—Sughrue Mion, PLLC

(57) ABSTRACT

An appliance 10 for large saphenous vein varix treatment comprises a stainless steel guide wire 1 provided on a distal end with a guide portion 11 and on a proximal end with a coupled portion 12, an absorption thread 2 connected to the proximal end coupled portion 12 of the guide wire 1, a transparent flexible bag 3 for containing the absorption thread 2, and a sterilization holding case 4 for containing the guide wire 1 and the transparent flexible bag 3 in a sterilized condition. Upon use, the sterilization holding case 4 is opened, a vein sclerosing agent is injected into the transparent flexible bag 3, and the vein sclerosing agent is impregnated into the absorption thread 2.

11 Claims, 3 Drawing Sheets

GREAT SAPHENOUS VEIN VARIX TREATMENT TOOL

TECHNICAL FIELD

This invention relates to an appliance for large saphenous vein varix treatment and more particularly relates to an appliance to be used upon an extraction surgery of a large saphenous vein.

BACKGROUND ART

Heretofore, in a treatment of a large saphenous vein varix and in particular an extraction surgery, a vein-extracting method and a vein-sclerosing method have been adopted.

The vein-extracting method comprises the steps of applying a lumber vertebrae anesthesia or a general anesthesia to a patient, stripping a portion joined between the large saphenous vein of the groin and the femora vein, clipping the large saphenous vein, inserting a stopper into the interior of the large saphenous vein, attaching a head to a wire detachably in accordance with a size of a vein varix, and extracting the large saphenous vein by drawing the wire. At this time, since branches of the vein blood vessel are broken, a doctor and assistances manually apply an astriction to the blood vessel. Then, a skin on the varix blood vessel is cut by 3–5 mm and the varix blood vessel is removed by using cutting pliers. The vein-extracting method requires a relatively long period of time and cannot be applied to an easily bleeding case. In addition, when the anesthesia becomes void after the surgery, the patient will be subject to a pain.

The vein-sclerosing method includes the steps of injecting a vein-sclerosing agent into a vein varix blood vessel in a patient to cause an occlusion in the vein and sclerosing the vein varix blood vessel to cease a blood flow. A little amount of the vein-sclerosing agent is injected into every several positions in the varix. The agent can be injected into an outpatient at several times. If a great amount of the vein-sclerosing agent is injected into the patient at a time, a deep part vein occlusion or a lung embolus-pathy may occur with the large saphenous vein varix. If the agent is injected into an artery by mistake, mortification will occur in a skin or a muscle.

In order to inject the vein-sclerosing agent into a check valve of a part flowing to the femora vein in the large saphenous vein, an ultrasonic wave is used as an assistant means. However, this requires a very high mastery.

On the other hand, a skin may be cut by using a local anesthesia and the blood vessel flowing to the femora vein in the large saphenous vein is nipped at the same time. In this case, a large branched blood vessel must be nipped after cutting the skin. Although this method is simple, there are many reoccurrences and a hypodermic chromatosis may occur.

Although the vein-sclerosing method is simple and excellent, a suitable medical appliance has not been developed. Accordingly, the method is not available in view of establishment of safety, prevention of reoccurrence, adverse reaction after treatment.

DISCLOSURE OF INVENTION

An object of the present invention is to provide an appliance for large saphenous vein varix treatment that can utilize the vein-sclerosing method safely and positively.

An appliance for large saphenous vein varix treatment in accordance with the present invention comprises: a stainless steel guide wire provided on a distal end with a guide portion and on a proximal end with a coupled portion; an absorption thread connected to the proximal end coupled portion of the guide wire; a transparent flexible bag for containing the absorption thread; and a sterilization holding case for containing the guide wire and the transparent flexible bag in a sterilized condition.

The guide wire may be a stainless steel wire or a stainless steel wire coated with a plastic material. The guide portion for the distal end of the guide wire is made of a plastic material or a stainless steel and formed into a rounded shape or a snakehead-like shape. The proximal end of the guide wire may be connected to the distal end of the absorption thread by means of insertion or binding and the connected portion may be shaped into a coupled portion by an adhesive. The proximal end of the guide wire may be connected to the distal end of the absorption thread by means of a plug-in type connector. The transparent flexible bag is formed so that a sclerosing agent can be injected into the bag. The absorption thread is preferably made of a porous material that can absorb and contain a sclerosing agent. The sclerosing agent may be POLIDCANOL (trade name) and it is injected into a transparent flexible bag.

In the appliance for large saphenous vein varix treatment of the present invention, the sterilization holding case is opened, the sclerosing agent is injected into the transparent flexible bag, and the bag is softened to uniformly impregnating the sclerosing agent into the absorption thread as much as possible. Then, the appliance is ready with operation for large saphenous vein varix treatment.

In a real large saphenous vein varix treatment, the appliance ready for the treatment is put near a doctor, the guide wire is inserted into a given large saphenous vein, and the absorption thread in which the sclerosing agent is impregnated is inserted into the large saphenous vein while the guide wire is drawing from the large saphenous vein. After drawing the guide wire completely, the absorption thread is cut off from the guide wire and only the absorption thread is left in the large saphenous vein. The absorption thread is drawn from the large saphenous vein after 24 hours have elapsed.

BEST MODE FOR CARRYING OUT THE INVENTION

By referring now to FIGS. 1 to 4, a preferred embodiment of an appliance for large saphenous vein varix treatment will be described below.

Figure 1:
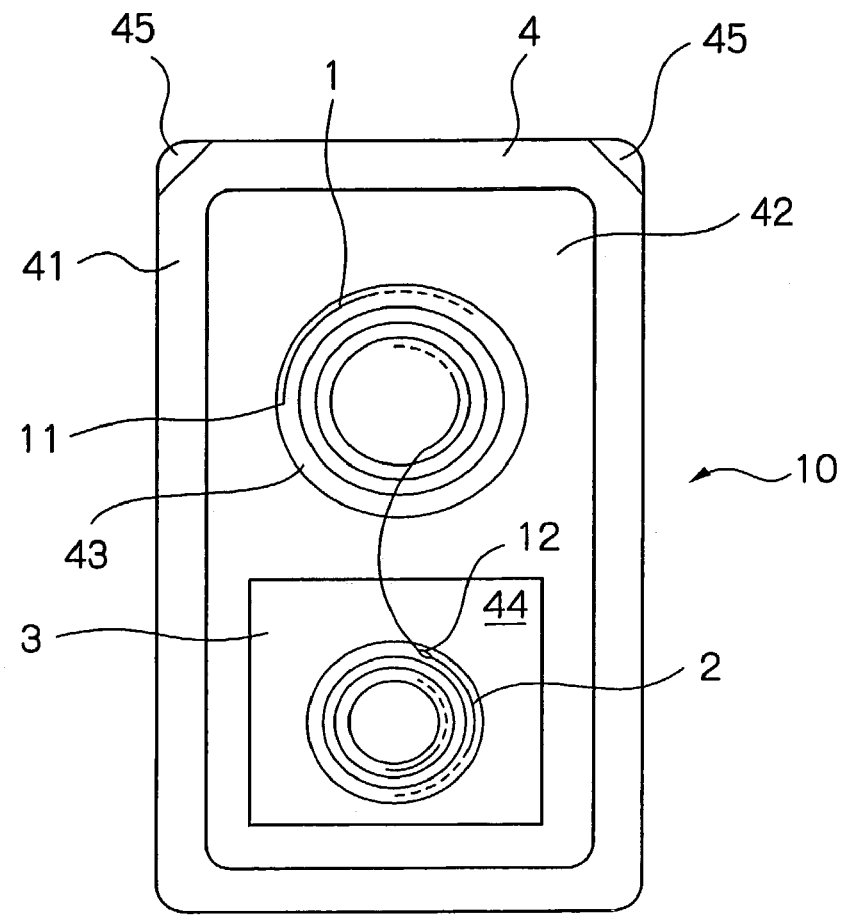
FIG. 1 is a plan view of an appliance for large saphenous vein varix treatment of the present invention.
Figure 2:
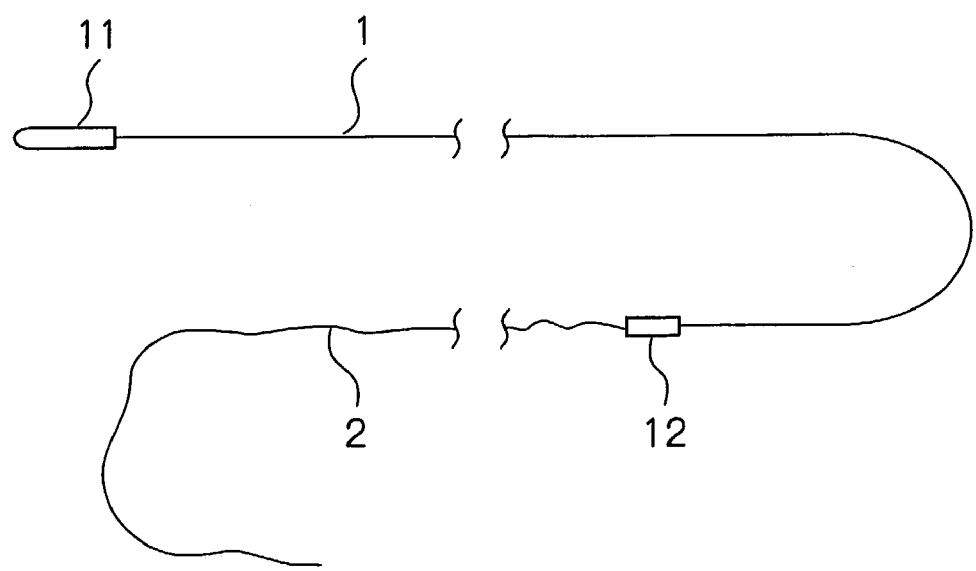
FIG. 2 is a plan view of a coupled assembly including a guide wire and an absorption thread, illustrating the coupled assembly taken out from the appliance.
Figure 3:
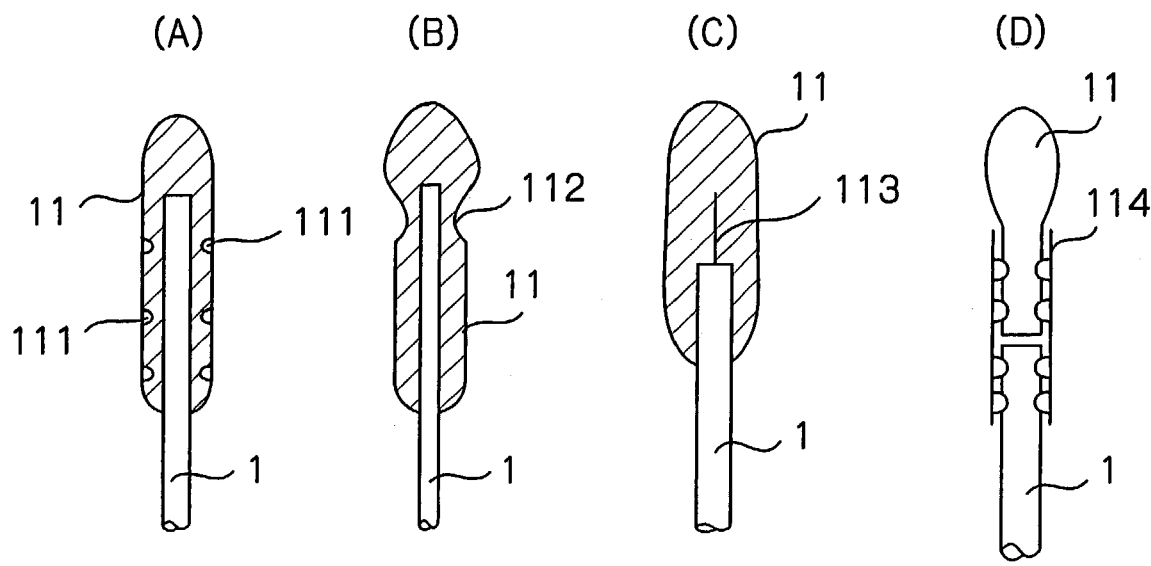
FIGS. 3A, 3B, 3C, and 3D are longitudinal sectional views of various kinds of end guide heads of the guide wires.
Figure 4:
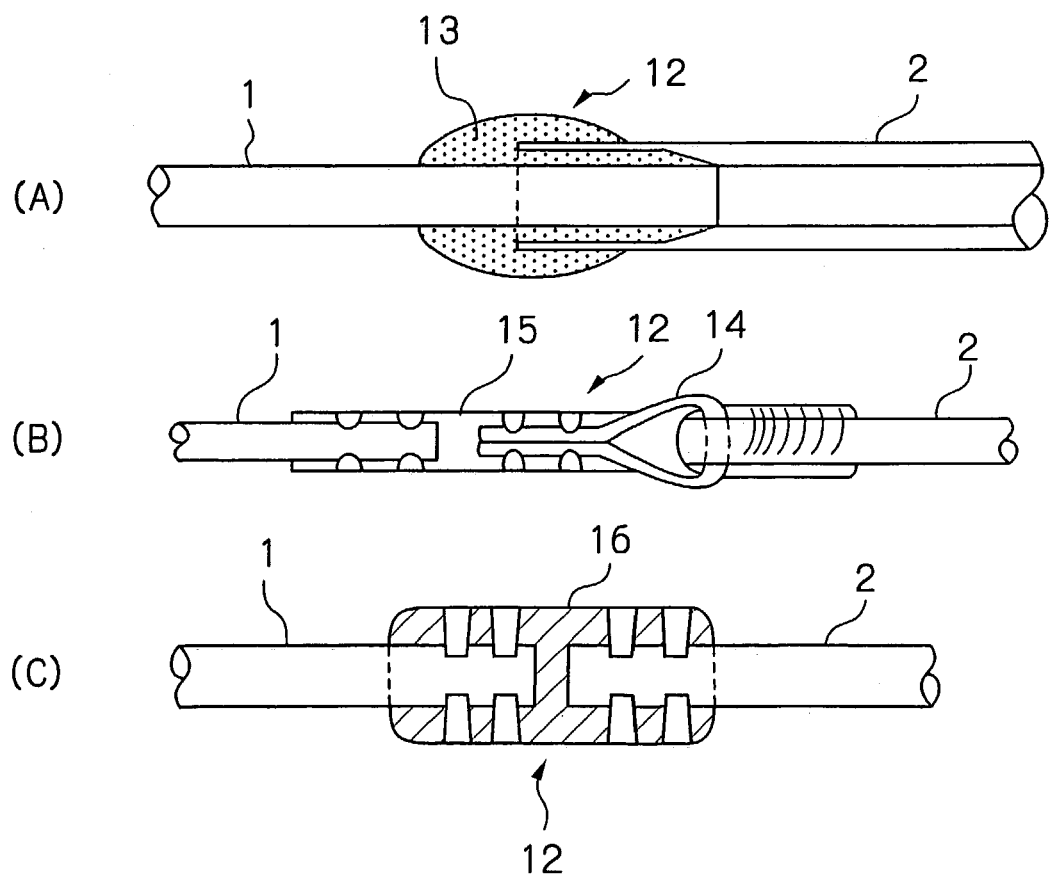
FIGS. 4A, 4B, and 4C are longitudinal sectional views of various kinds of coupled portions of the guide wires and absorption threads.

As shown in FIGS. 1 and 2, an appliance 10 for large saphenous vein varix treatment in accordance with the present invention mainly comprises a stainless steel guide wire 1 provided on a distal end with a guide portion 11 and on a proximal end with a coupled portion 12, an absorption thread 2 connected to the proximal end coupled portion 12 of the guide wire 1, a transparent flexible bag 3 for containing the absorption thread 2, and a sterilization holding case 4 for containing the guide wire 1 and the transparent flexible bag 3 in a sterilized condition.

Figure 5:
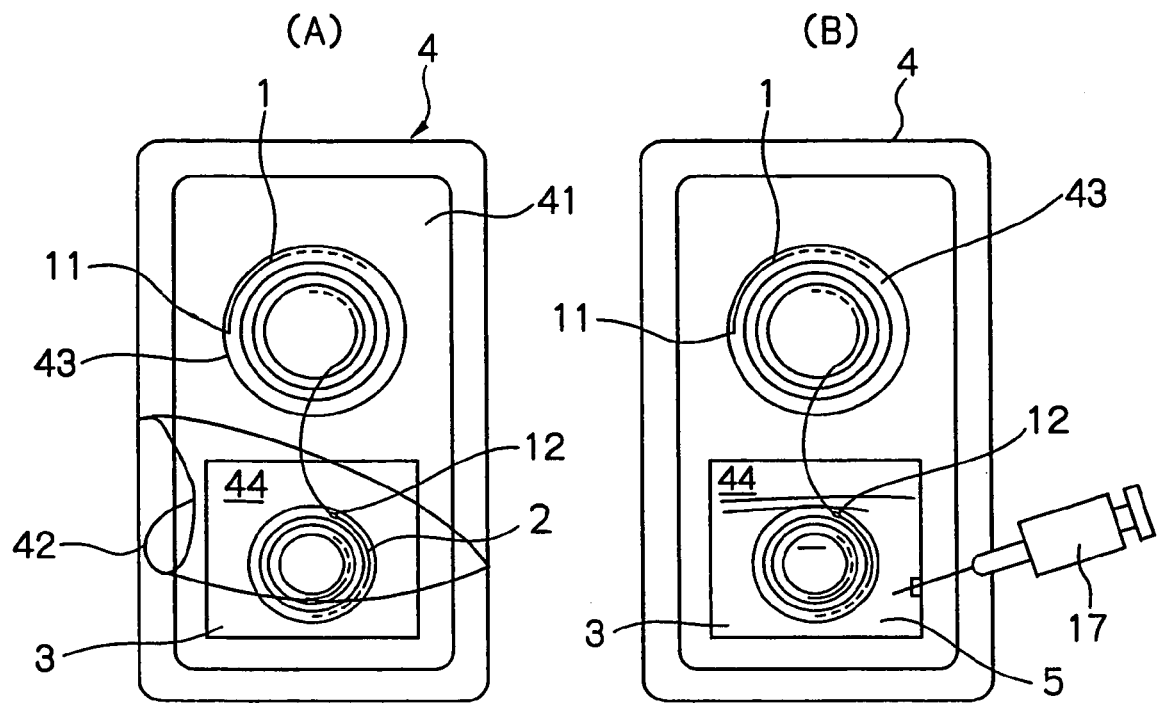
FIGS. 5A and 5B are plan views similar to FIG. 1, illustrating steps of preparing the appliance for large saphenous vein varix treatment.

The sterilization holding case 4, as best shown in FIG. 1 and FIG. 5A, includes a flat case body 41 and a transparent cover 42 covering the case body 41. The cover 42 is adhered to the case body 41 so that the cover can be easily peeled off from an upper corner portion 45 of the case body 41. The case body 41 is provided with containing recesses 43 and 44 for containing the guide wire 1 and transparent flexible bag 3.

FIG. 2 is a plan view of a coupled assembly including the guide wire 1 and the absorption thread 2, illustrating the coupled assembly taken out from the appliance 10 for large saphenous vein varix treatment. The guide wire 1 may be a stainless steel wire or a stainless steel wire covered with a plastic resin material (for example, Parsonet Sonde (trade name) being commercially available). It is preferable to prepare the guide wire 1 having various sizes of 0.8–1.5 mm in diameter and 500–1000 mm in length. It is also preferable to make markers (not shown) on the guide wire 1 at a given interval (for example, 100 mm). The absorption thread 2 may be a usual thread for operation such as cotton, nylon, polypropylene, polyester, polyvinyl or the like and in particular preferably a porous material having high absorption and impregnation characteristics for vein sclerosing agent. For example, ETIBOND EXCEL 5 (trade mane) or PDS-KORDEL (BPT-1) (trade name) sold commercially by ETHICON Co. is preferable. The absorption thread 2 has substantially the same diameter and length as those of the guide wire 1.

The absorption thread 2 is sealed in the transparent flexible bag 3 beforehand and a vein sclerosing agent 5 is injected into the bag 3 by an injector 17 when using it (see FIG. 5B). The vein sclerosing agent 5 is preferably ETHOXYSCLEROL (trade name) sold commercially by KAIGEN Co.

A distal end guide portion 11 of the guide wire 1 is made of a plastic material or stainless steel. As shown in FIGS. 3A, 3B, 3C, and 3D, connection between the distal end guide portion 11 and the guide wire 1 is made by inserting an end of the guide wire 1 into the portion (head) 11 and applying several caulking recesses 111 to a periphery of the portion 11 (FIG. 3A), by applying a deep caulking recess 112 to the portion 11 (FIG. 3B), by coupling the portion 11 and guide wire 1 to each other by a fine wire 113 (FIG. 3C), or by fitting a sleeve 114 on a rear end of the portion 11 and an front end of the guide wire 1 and applying several caulking recesses to the sleeve 114 (FIG. 3D). The distal end guide portion 11 has preferably 2–2.5 mm in diameter and 5–20 mm in length. The distal end guide portion 11 is formed into a round shape at the distal end and proximal end (FIGS. 3A to 3C) or a shape of a head of a snake at a distal end (FIG. 3D) not to injure an inner wall of a blood vessel.

As shown in FIGS. 4A, 4B, and 4C, a proximal end coupling-portion 12 of the guide wire 1 is formed by inserting a proximal end of the guide wire 1 into an end port of a hollow absorption thread 2 and adhering their peripheries by adhesive 13 (FIG. 4A), by coupling the proximal end of the guide wire 1 and the distal end of the absorption thread 2 to each other by a looped wire 14 and coupling the distal end of the looped wire 14 to a connector 15 (FIG. 4B), or by inserting the proximal end of the guide wire 1 and the distal end of the absorption thread 2 into opposite ports in a plug-in type connector 16 and applying several caulking recesses to the connector 16 (FIG. 4C). In any cases, it is preferable to apply an adhesive to the connected portion or to regulate the caulking recesses not to cause any stepped portions on the connected part.

In the appliance 10 for large saphenous vein varix treatment of the present invention, the sterilization holding case 4 is opened (FIG. 5A), the scierosing agent 5 is injected into the transparent flexible bag 3. The bag 3 is softened to uniformly impregnating the sclerosing agent 5 into the absorption thread 2 as much as possible. Then, the appliance 10 is ready with operation for large saphenous vein varix treatment.

In a real large saphenous vein varix treatment, the applicance 10 ready for the treatment is put near a doctor, the guide wire 1 is inserted into a given large saphenous vein, and the absorption thread 2 in which the scierosing agent 5 is impregnated is inserted into the large saphenous vein while the guide wire 1 is drawing from the large saphenous vein. After drawing the guide wire 1 completely, the absorption thread 2 is cut off from the guide wire 1 and only the absorption thread 2 is left in the large saphenous vein. The absorption thread 2 is drawn from the large saphenous vein after 24 hours have elapsed. The sclersoing agent 5 impregnated in the absorption thread 2 is completely solidified in the large saphenous vein.

EXAMPLE 1

Figure 6:
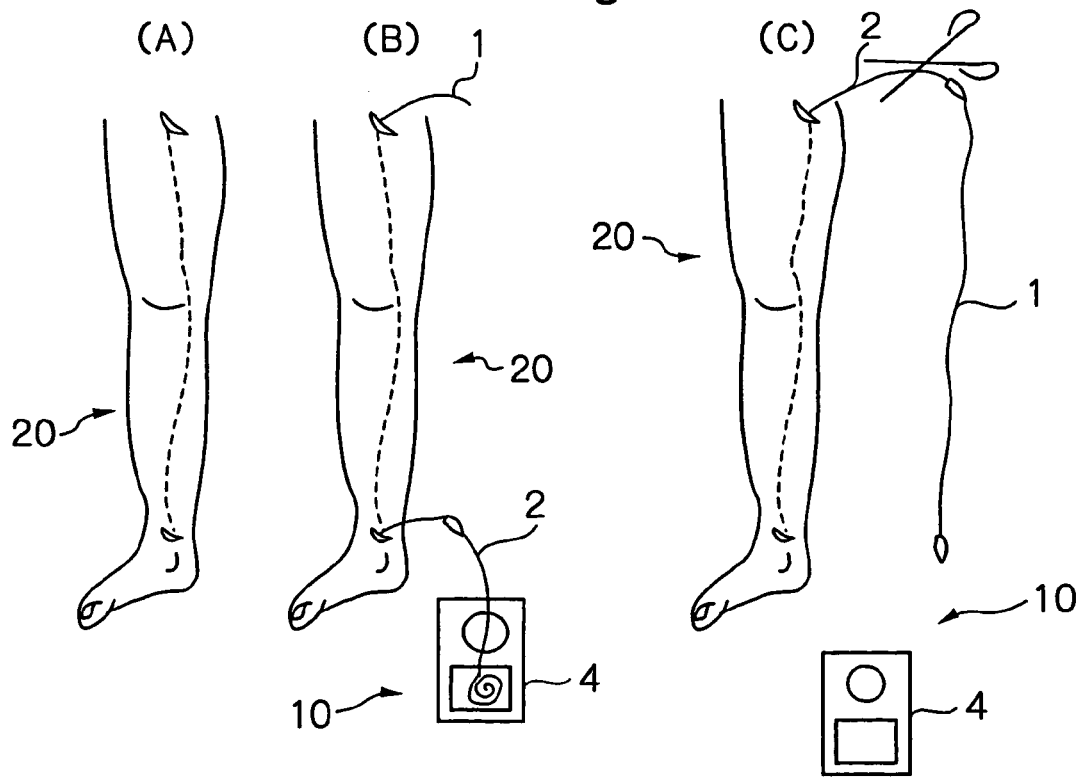
FIGS. 6A, 6B, and 6C are explanation views of examples of using the appliance for large saphenous vein varix treatment.

Referring to FIGS. 6(A), 6(B), and 6(C), an example, in which the appliance 10 for large saphenous vein varix treatment of the present invention is really used, will be explained below.

Firstly, a local anesthesia was applied to a desired part of a patient 20, a femoral vein combining-site of a large saphenous vein was highly bound FIG. 6(A), and the guide wire 1 was inserted into the large saphenous vein extending from an ankle to a groin FIG. 6(B). Secondly, the ethibond thread 2 impregnating the ethoxysclerol was inserted into the large saphenous vein while the guide wire 1 was being drawn FIG. 6(B). After the guide wire 1 was completely drawn from the large saphenous vein, the ethibond was thread 2 was cut off from the guide wire 1 and only the ethibond thread 2 was left in the vein FIG. 6(C). After 24 hours had elapsed since the operation was completed, the ethibond thread 2 that had a slidable property had been easily drawn from the large saphenous vein of the outpatient.

Thereafter, the lumens in the large saphenous vein and penetrating branches were completely closed and thus the same treatment effect as the vein-drawing treatment (stripping treatment) was obtained.

The other sublimes vein varices were subjected to the vein-extracting surgery after applying a local anesthesia to the outpatient. Any recrudescence has not been found.

INDUSTRIAL APPLICABILITY

The appliance for large saphenous vein varix treatment can be utilized in a small saphenous vein as well as a large saphenous vein.

What is claimed is:
1. An appliance for large saphenous vein varix treatment comprising:

a guide wire provided on a distal end with a guide portion and on a proximal end with a coupled portion; an absorption thread connected to said proximal end coupled portion of said guide wire; a flexible bag for containing said absorption thread; and a sterilization holding case for containing said guide wire and said flexible bag therein in a sterilized condition;

wherein said flexible bag is separate from said holding case; and wherein the guide wire has a length of 500–1000 mm.

2. An appliance for large saphenous vein varix treatment according to claim 1, wherein said guide portion for the distal end of said guide wire is made of a plastic material or a stainless steel and formed into a rounded shape or a snakehead-like shape.

3. An appliance for large saphenous vein varix treatment according to claim 1, wherein the proximal end of said guide wire is connected to the distal end of said absorption thread by means of insertion or binding and the connected portion is shaped into a coupled portion by an adhesive or a caulking work.

4. An appliance for large saphenous vein varix treatment according to claim 1, wherein the proximal end of said guide wire is connected to the distal end of said absorption thread by means of a plug-in type connector.

5. An appliance for large saphenous vein varix treatment according to claim 1, wherein said flexible bag is formed so that a scierosing agent can be injected into said bag.

6. An appliance for large saphenous vein varix treatment according to claim 1, wherein said absorption thread is made of a porous material that can absorb and contain a scierosing agent.

7. An appliance for large saphenous vein varix treatment according to any one of claims 1 to 6, wherein said guide wire is a stainless steel wire or a stainless steel wire coated with a plastic material.

8. An appliance for large saphenous vein varix treatment according to claim 1, wherein a distal end of said guide portion is blunt.

9. The appliance according to claim 8, wherein said blunt distal end of said guide portion has a round shape.

10. The appliance according to claim 8, wherein said blunt distal end of said guide portion has the shape of a head of a snake.

11. An appliance for large saphenous vein varix treatment according to claim 1, wherein the guide wire is covered with a plastic resin material.

* * * * *